United States Patent [19]
Carter et al.

[11] Patent Number: 6,010,486
[45] Date of Patent: Jan. 4, 2000

[54] RETRACTING NEEDLE SYRINGE

[75] Inventors: Michael J. Carter, Somerville; Richard Caizza, Barry Lakes, both of N.J.

[73] Assignee: Becton Dickinson and Company, Frankin Lakes, N.J.

[21] Appl. No.: 09/216,561

[22] Filed: Dec. 18, 1998

[51] Int. Cl.[7] ................................................. A61M 5/00
[52] U.S. Cl. .......................................... 604/195; 604/110
[58] Field of Search .................................. 604/195, 198, 604/110, 192, 187, 263, 218

[56] References Cited

U.S. PATENT DOCUMENTS

| | | | |
|---|---|---|---|
| 4,687,467 | 8/1987 | Cygielski | 604/110 |
| 4,838,863 | 6/1989 | Allard et al. | 604/110 |
| 4,838,869 | 6/1989 | Allard | 604/195 |
| 5,019,044 | 5/1991 | Tsao | 604/110 |
| 5,049,133 | 9/1991 | Pascual | 604/110 |
| 5,053,010 | 10/1991 | McGary et al. | 604/110 |
| 5,090,962 | 2/1992 | Landry et al. | 604/110 |
| 5,180,369 | 1/1993 | Dysarz | 604/110 |
| 5,180,370 | 1/1993 | Gillespie | 604/110 |
| 5,201,710 | 4/1993 | Caselli | 604/110 |
| 5,395,337 | 3/1995 | Clemens et al. | 604/110 |
| 5,407,436 | 4/1995 | Toft et al. | 604/195 |
| 5,769,822 | 6/1998 | McGary et al. | 604/110 |

FOREIGN PATENT DOCUMENTS 2 197 792A   6/1988   United Kingdom .

OTHER PUBLICATIONS

Article entitled: "Safer Syringes Boost Molder Opportunities" by Carl Kirkland, pp. 20–24, from Plastics World, Aug. 1993.

*Primary Examiner*—John D. Yasko
*Attorney, Agent, or Firm*—Keith J. McWha

[57] ABSTRACT

A retracting needle syringe is described which allows safe and easy disposal of a syringe and prevents re-use of the syringe by destroying the plunger rod and needle hub and retracting the needle into the plunger rod. Once the safety feature is activated, positive or negative pressure in the barrel to draw out medication is defeated. The retracting needle safety feature requires only an increase of force along the same line of action as the injection stroke. This allows for safe, one-handed injection, which is critical in some situations. The retracting needle syringe of the present invention also minimizes the amount of wasted medication because the plunger rod incorporates a plunger tip that occupies the entire volume inside the barrel. Because the retracting needle syringe uses standard luer-lok fittings, it can be used with a variety of standard needles that do not have retracting cannula. This gives the healthcare professional or patient the ability to use a large gauge needle to fill the syringe from a vial or other container before attaching the safety needle for injection. Lastly, the plunger can be completely encapsulated by the barrel upon activation of the retracting needle syringe safety feature which will prevent re-use of the syringe and allow for safe and easy disposal.

34 Claims, 9 Drawing Sheets

RETRACTING NEEDLE SYRINGE

FIELD OF INVENTION

This invention relates generally to a medical device with safety sharps features. More particularly, this invention relates to a syringe for medical use that has a retracting needle feature which allows safe and easy disposal of the syringe and prevents re-use by destroying the plunger rod and needle hub and retracting the needle into the plunger rod.

BACKGROUND OF THE INVENTION

Hypodermic syringes are well known to be used to deliver fluids like medication, for example, to patients. A traditional hypodermic syringe typically includes a syringe barrel having opposed proximal and distal ends. A cylindrical chamber wall extends between the ends and defines a fluid-receiving chamber. The proximal end of the traditional syringe barrel is substantially open and receives a plunger in sliding fluid tight engagement. The distal end of the traditional syringe barrel includes a passage communicating with the chamber. A needle cannula is mounted to the distal end of the traditional syringe barrel such that the lumen of the needle cannula communicates with the passage and the chamber of the syringe barrel. Movement of the plunger in the proximal direction draws fluid through the lumen of the needle cannula and into the chamber. Movement of the plunger in a proximal to distal direction urges fluid from the chamber and through the lumen of the needle cannula.

In recent years, considerable effort has been invested in providing for a syringe for medical use that is both safe and easy to dispose and non-reusable. Some of these syringes include a retractable needle safety feature. However, these mechanisms are somewhat complex, difficult to use and can increase manufacturing costs while decreasing efficiency in the manufacturing process. For example, a retractable needle safety syringe of one type requires the user to push the plunger fully into the barrel until engagement is felt and an audible click is heard. The user then opens a safety clip at the distal end of the barrel. The plunger is then fully retracted. This brings the needle back into the syringe barrel. The plunger is then snapped off and inserted into the open barrel, sealing the needle within the syringe for safe disposal.

Another design incorporates a plunger being pushed forward and rotated. An integrally molded spring locks into the needle hub. The plunger rod is then drawn rearward, and then tension in a spring is released to angle the hub and the needle to the side, thereby disarming the syringe.

Yet, another retractable safety syringe comprises, a plunger, a barrel, an elastomeric piston, hub, and a needle. This design allows a used needle to be withdrawn inside the syringe barrel following use and automatically tilts it sideways. There are conforming luer locks on the barrel and needle hub that allow the needle hub to engage and disengage inside the barrel. Dart-shaped cleats on the inner circumference of the hub selectively engage complimentary cleats on the plunger tip. The plunger can be freely moved back and forth until the needle retraction is desired. At that time the plunger is pushed forward into the needle hub and rotated counterclockwise camming the plunger into the hub and locking the two together. The camming action simultaneously compresses an integrally molded spring on the plunger tip. Continued rotation disengages the hub and releases the coupled components to be drawn rearward. The plunger is then retracted until it is stopped by tabs on the barrel that prevent rearward exit. As the needle clears the mouth of the barrel, the compressed spring is released, deflecting the needle to the barrel sidewall. Needle retention is achieved and the needle is blocked by the forward barrel wall allowing the disarmed syringe with the used needle to be safety stored in the barrel before disposal.

Each of these proposed constructions of retractable needle syringes has certain disadvantages. Many of them have complicated working parts and require complicated procedures to activate the safety mechanisms. In addition to these mechanisms being somewhat complex, they also increase manufacturing costs due to their multiple component configuration, and decrease efficiency in the manufacturing process.

Therefore, a need exists in the art which allows safe and easy disposal of a syringe and prevents re-use. The device should allow use of a variety of standard needles for filling purposes.

SUMMARY OF THE INVENTION

A retracting needle syringe for medical use which allows safe and easy disposal of the syringe and prevents re-use while having minimal components comprises a syringe barrel, a plunger rod, and a needle assembly. The needle assembly is attached to the distal end of the syringe barrel. The needle assembly comprises an inner hub, an outer hub and a spring. The inner hub has a frangible portion and a piercing member fixably attached. A spring is disposed over the piercing member. The inner hub is engaged inside the outer hub for providing compression to the spring.

The plunger rod has a plunger tip and a chamber. The chamber has a closed end and an open end. The open end is sealed by the plunger tip. The plunger rod, chamber, and plunger tip are all one piece.

A severing means is adjacent to the open end of the chamber for providing passage into the chamber through the plunger tip. Upon fully depressing the plunger rod and applying distally directed axial force, the frangible portion of the inner hub breaks and the plunger tip dislodges by the severing means thereby allowing the spring to move the piercing member to enter the chamber.

A stopper is attached to the plunger rod and disposed around the plunger tip such that the plunger tip is substantially uninterrupted by the stopper when the plunger tip is dislodged.

The severing means can be a cutting ring that is embedded in the distal end of the syringe barrel. The cutting ring has a single-edge blade. In another embodiment, the severing means is a frangible portion surrounding the plunger tip.

The frangible portion of the inner hub requires less force to break than the plunger tip such that the plunger tip breaks the frangible portion of the inner hub when the plunger is fully depressed and the plunger tip is dislodged by the severing means.

In the embodiment where the severing means is a frangible portion surrounding the plunger tip, the plunger tip is dislodged by the frangible portion surrounding the plunger tip when the plunger is fully depressed. The piercing member can enter the chamber by the force of the spring when the frangible portion of the inner hub breaks by the plunger tip when the plunger rod is fully depressed.

In the embodiment where the severing means is a cutting ring, the plunger tip is dislodged by action of the cutting ring when the plunger is fully depressed. Thus, the piercing member can enter the chamber by the force of the spring when the frangible portion of the inner hub breaks by the plunger tip when the plunger rod is fully depressed.

In both embodiments, the inner and outer hub are both dimensioned so that the outer diameter of the inner hub and the inner diameter of the outer hub provide a permanent press fit between both components. The frangible portion of the inner hub allows entry of the piercing member into the chamber when the plunger rod is fully depressed and the plunger tip is dislodged by the severing means.

A snap fitting on the proximal end of the syringe barrel provides for locking the plunger rod by the barrel when the plunger rod is fully depressed. Thus, the present invention protects against re-use.

DETAILED DESCRIPTION

Figure 1:
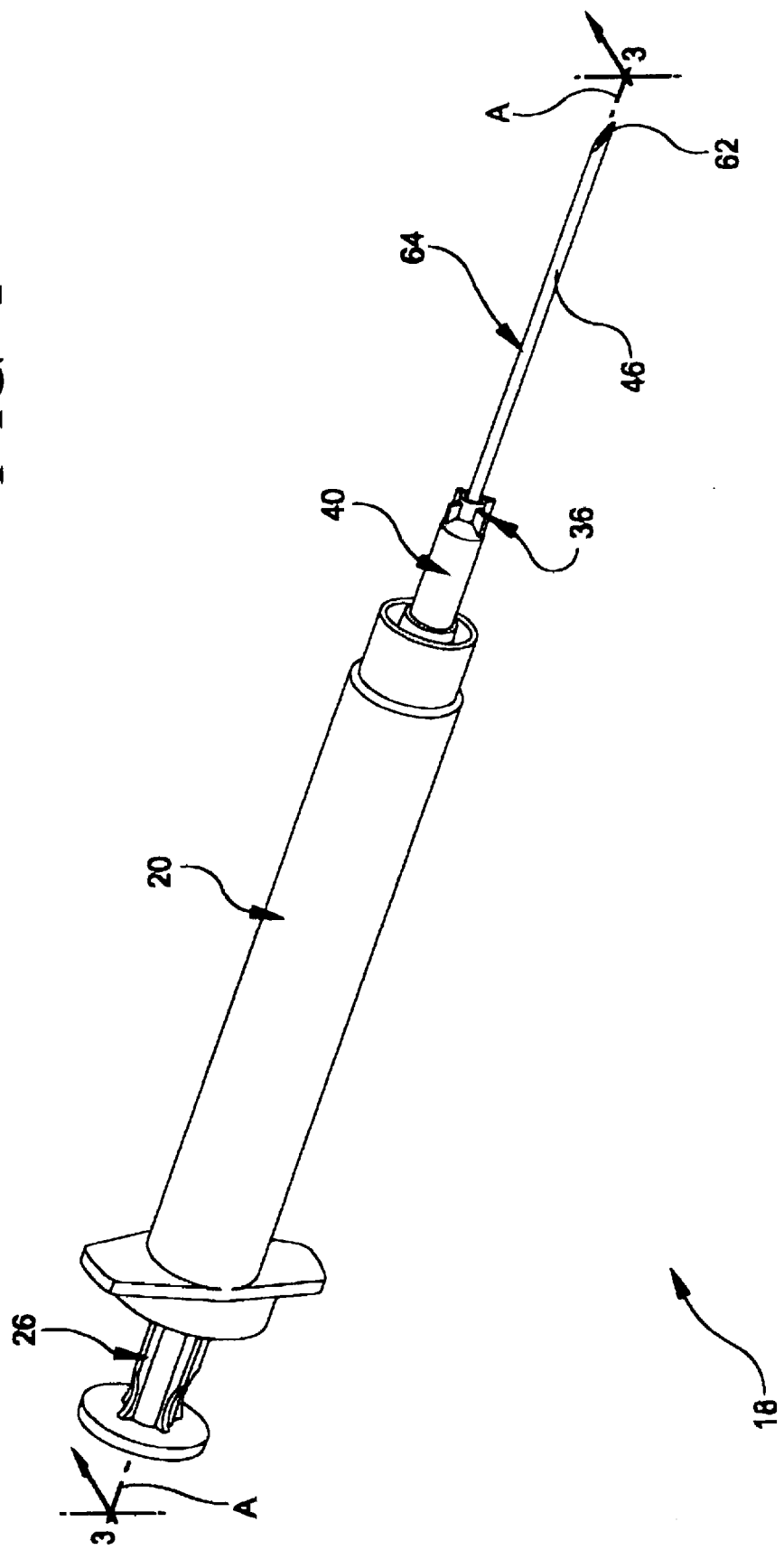
FIG. 1 is a side view of the present invention.

While this invention is satisfied by embodiments in many different forms, there is shown in the drawings and will be herein described in detail preferred embodiments of the invention with the understanding that the present disclosure is to be considered exemplary of the principles of the invention. It is not intended to limit the scope of the invention to these embodiments illustrated. The scope of the invention will be measured by the appended claims and their equivalents.

Figure 2:
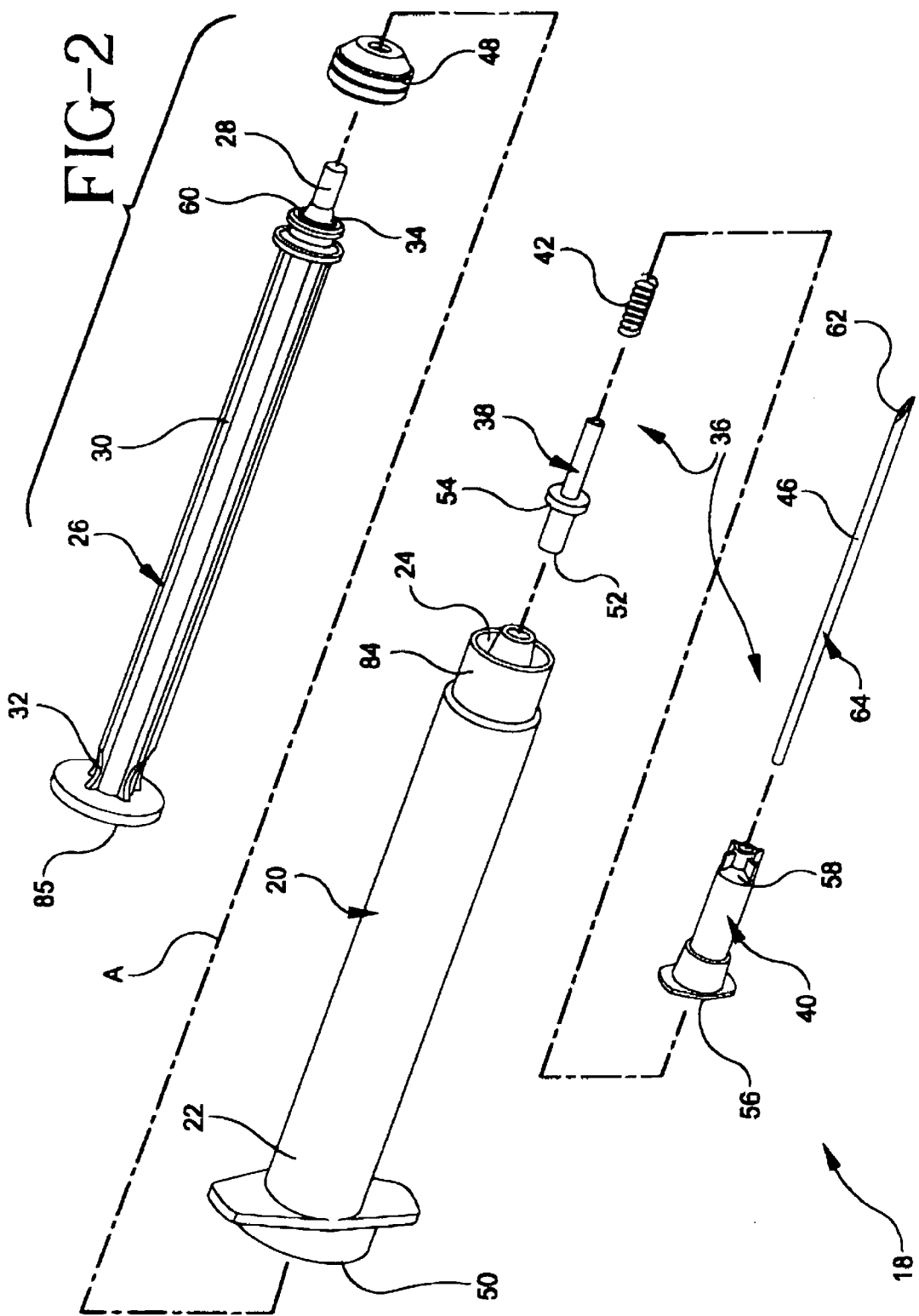
FIG. 2 is an exploded view in perspective of the present invention.

Adverting to the drawings, FIGS. 1–9 illustrate the present invention of a retracting needle syringe 18. Shown in FIGS. 1 and 2 is a syringe barrel 20 for holding liquid. This liquid may be medication, saline solution, flush solution or any other type of injectable liquid used for medical purposes. The barrel has a proximal end 22 and a distal end 24. A plunger rod 26 is disposed in the barrel and has a plunger tip 28. The plunger rod also has a chamber 30 within. The chamber has a closed end 32 and an open end 34. The open end is preferably sealed by the plunger tip. Preferably, the plunger rod is molded as one-piece comprising the rod, the plunger tip and the chamber. The plunger tip can be hermetically sealed to prevent the entry of air or liquid into the plunger rod with the plunger tip, chamber, and the plunger rod made of one unitary piece. The sealed plunger rod allows the plunger to create positive or negative pressure in the barrel to draw out and inject the liquid. Once this plunger tip is broken, positive or negative pressure in the barrel to draw out and inject liquid is defeated and the syringe cannot be used. The plunger rod also defines an axis "A" shown in FIGS. 3 and 5.

Figure 8:
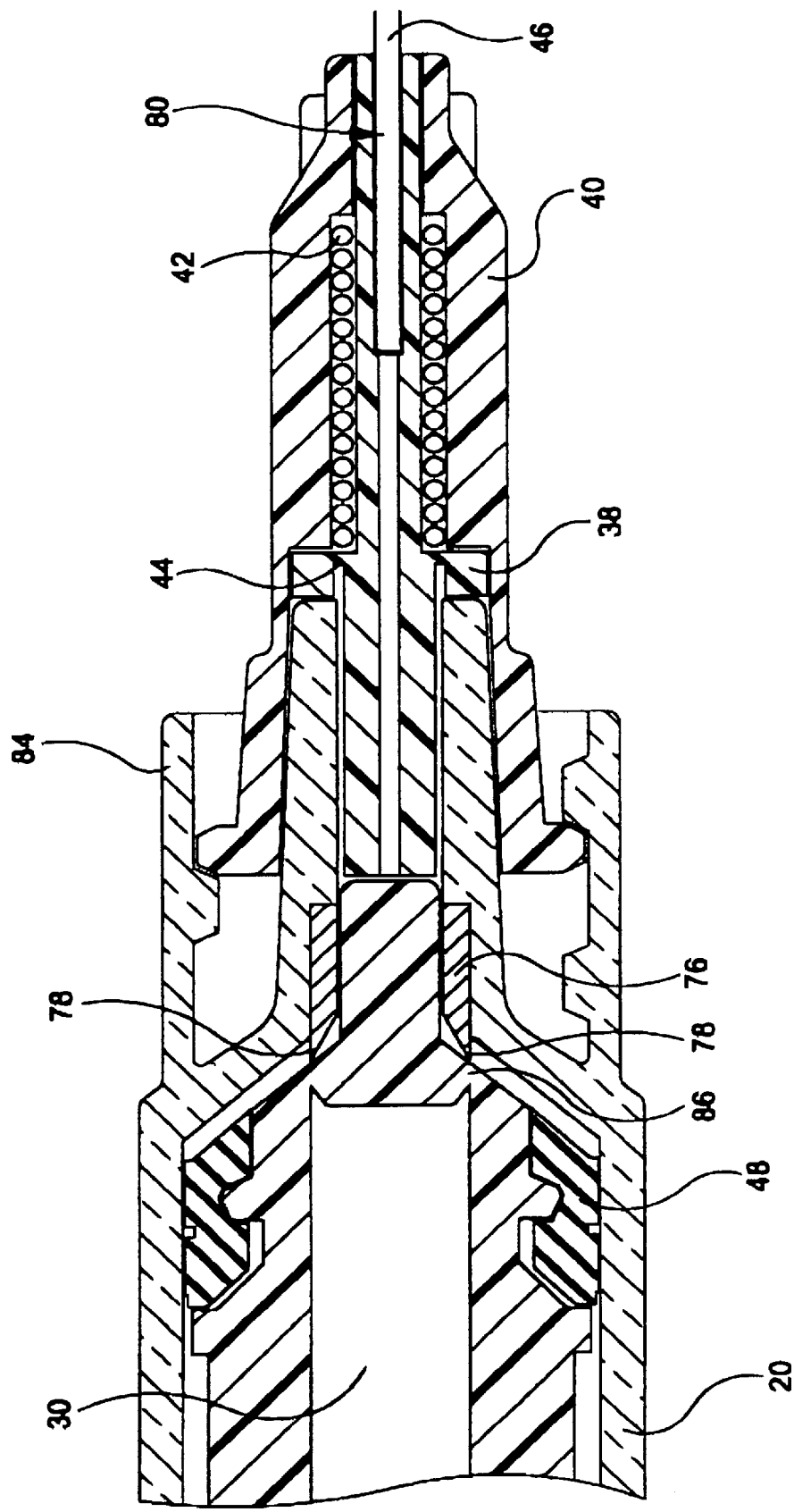
FIG. 8 is an enlarged cross-sectional view of the present invention where the severing means is a cutting ring.
Figure 9:
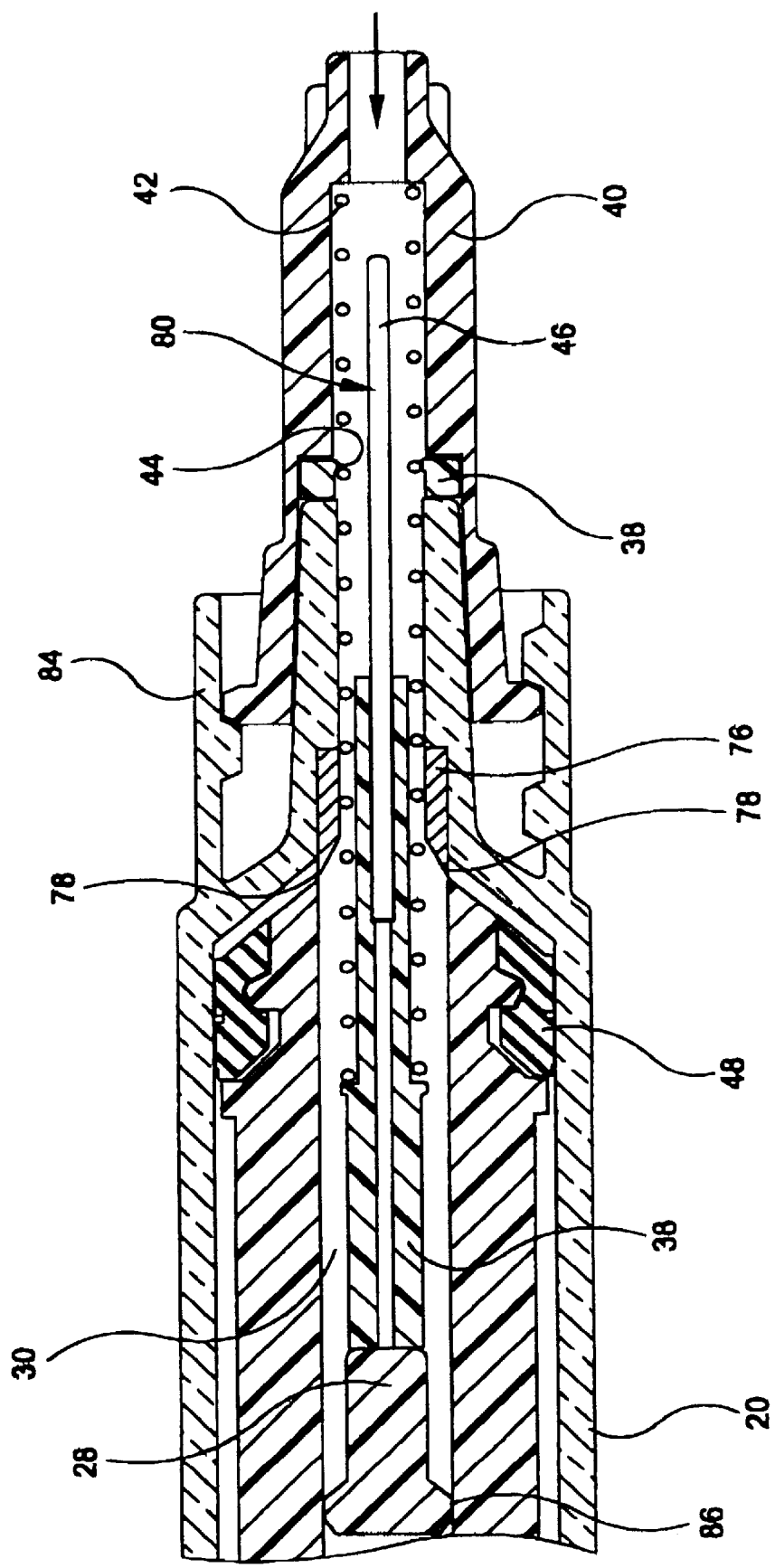
FIG. 9 is an enlarged cross-sectional view of the present invention illustrating the function of the severing means in FIG. 8.

Needle assembly 36 is attached to the distal end of the barrel. The needle assembly can be attached by several methods known by one skilled in the art. These attachment methods include, but are not limited to, heat welding, heat staking, adhesive bonding, ultrasonic welding, in-mold assembly techniques, and press or snap fittings. Preferably, the needle assembly is removably attached to the distal end of the barrel. The needle assembly has an inner hub 38, an outer hub 40 and a spring 42. The inner hub has a frangible portion 44 and a piercing member 46 fixably attached. The spring is disposed over the piercing member. Preferably, the piercing member has a sharpened distal end 62 and is a needle cannula 64. However, it may be blunt as in the case of a blunt cannula 80 as shown in FIGS. 8 and 9 which are for intravenous injection ports. The piercing member may also be any other type of point at the distal end which allows the liquid to be injected. The inner hub is engaged inside the outer hub to provide compression to the spring. Because the barrel preferably uses the standard ISO number 594-1 and 594-2 luer lock fitting 84, and the needle assembly is removably attached, the present invention can be used with a variety of standard needles that do not have retracting cannula. This gives the end user the ability to use a large gauge standard needle to fill the syringe from a vial or other container before attaching the needle assembly for injection. The needle assembly can also be designed into a wide range of syringe and needle sizes. Thus, the present invention of the retracting needle syringe allows the use of a variety of standard needles that do not have retracting cannula.

A severing means is also included in the retracting needle syringe. Severing means is adjacent to the open end of the chamber. Severing means provides passage into the chamber by dislodging the plunger tip when the plunger rod is fully depressed along the axis "A". One of the advantages of the present invention is that only an increase of force of the plunger rod along the same line of action as the injection stroke is required to retract the piecing member. The activation of the needle assembly to allow the piercing member to enter the chamber only requires an increase of force of the plunger rod along axis "A" using a one-handed distally directed axial force. This activation technique allows for safe, one-handed injection, which is critical in some healthcare situations. When the plunger rod is fully depressed, the frangible portion of inner hub breaks unsecuring and allowing retraction of the piercing member and the plunger tip is dislodged by severing means, thereby allowing the piercing member to enter the chamber. The piercing member is maintained in the chamber by either the force of the uncompressed spring or by the larger diameter of the first fracture point 86 of the plunger tip.

Preferably, the retracting needle syringe has a frangible portion of the inner hub that requires less force to break than the plunger tip such that the plunger tip breaks the frangible portion of the inner hub when the plunger rod is fully depressed and the plunger tip is dislodged by the severing means. Once the plunger tip is dislodged the syringe cannot be reused because positive or negative pressure generated by the plunger rod to draw out or inject fluid is now defeated. Preferably, when the frangible portion of the inner hub is broke, the needle assembly cannot be re-used because the spring can now move or retract the piercing member. The piercing member can preferably enter the chamber in the plunger rod when the plunger tip is dislodged by the severing means. Thus, only an increase of force of the plunger rod along the same line of action as the injection stroke, Axis "A", is required to retract the piecing member.

The retracting needle syringe also minimizes the amount of wasted fluid or medication after injection because the plunger tip occupies the entire volume inside the distal end of the barrel. Typically, prior art syringes create dead-space volume between the connection of the syringe and the needle hub. An advantage of the present invention is that this volume can be reduced by having the plunger tip on the plunger rod extend into the dead space volume thereby occupying the entire volume inside the barrel which minimizes the amount of wasted fluid or medication after injection. This waste is important to minimize especially when expensive medication such as dialysis-related erythropuietin, filgrastim or many of the new and proposed recombinant biologicals are used.

Typically, the retracting needle syringe has piercing member with sharpened distal end. The piercing member in this embodiment is a needle cannula 64, however, it need not be with a sharpened distal end. Such is the case where a blunt cannula 80 is used in the needle assembly as shown in FIGS. 8 and 9.

The syringe barrel of the retracting needle syringe is typically made of a thermoplastic material. Such a material can be but is not limited to polypropylene, polyethylene, polystyrene, polyethylene terephthalate, polybutylene terephthalate, polycarbonate, polyesters and various polyblends.

The retracting needle syringe can also have an additional element, a stopper 48 which is attached to the plunger rod and disposed around the plunger tip such that the plunger tip is preferably substantially uninterrupted by the stopper when the plunger tip is dislodged. The stopper allows the medication to move from the proximal end to the distal end of syringe barrel. However, the stopper is not always needed for such a function. Such is the case when the plunger rod is designed without the stopper and provides for moving the fluid from the proximal end to the distal end upon an injection stroke. In this embodiment, the plunger rod and syringe barrel are dimensioned to provide positive and negative pressure upon moving the plunger rod.

Figure 6:
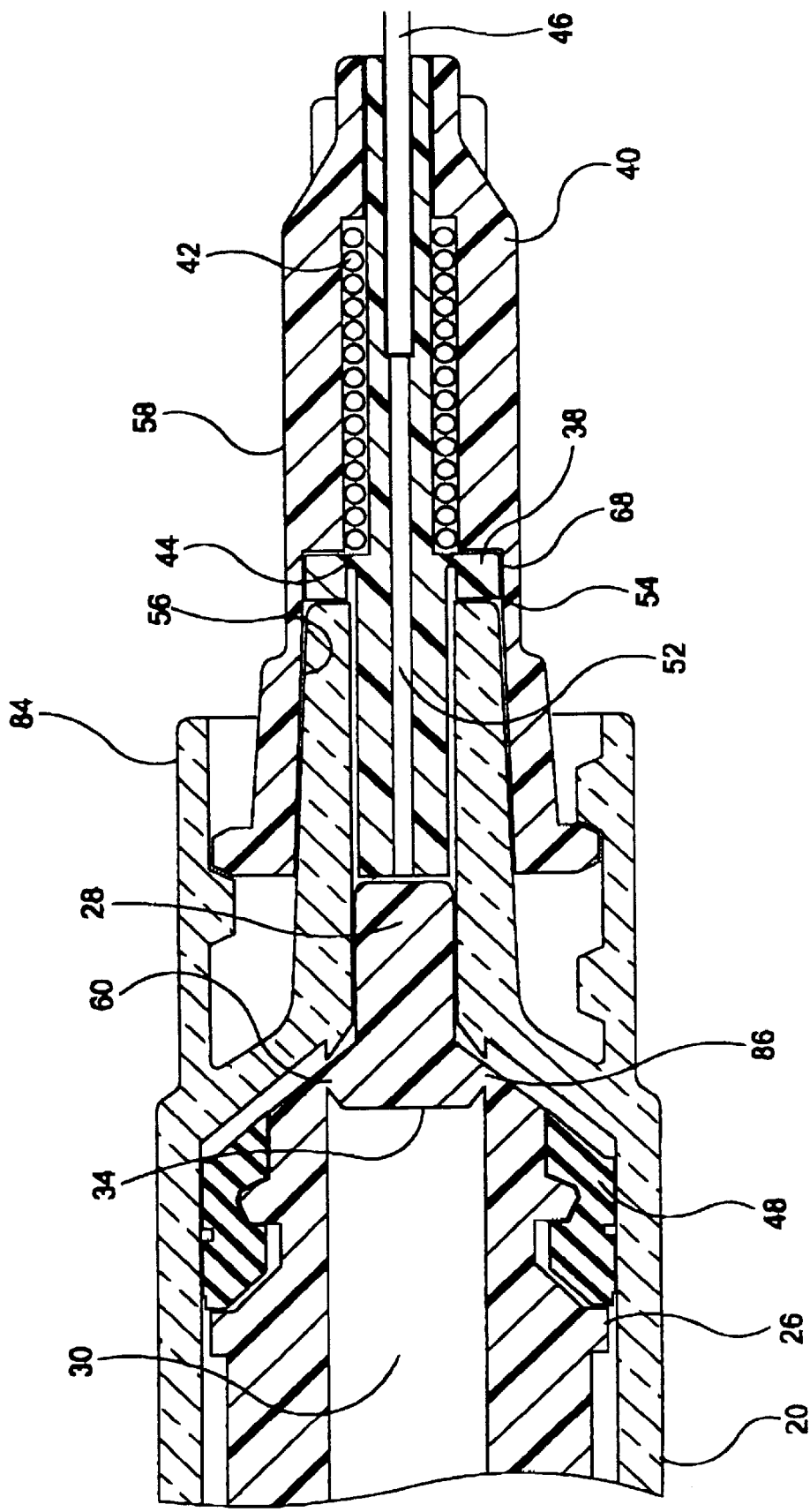
FIG. 6 is an enlarged cross-sectional view of the present invention where the severing means is a frangible portion surrounding the plunger tip.
Figure 7:
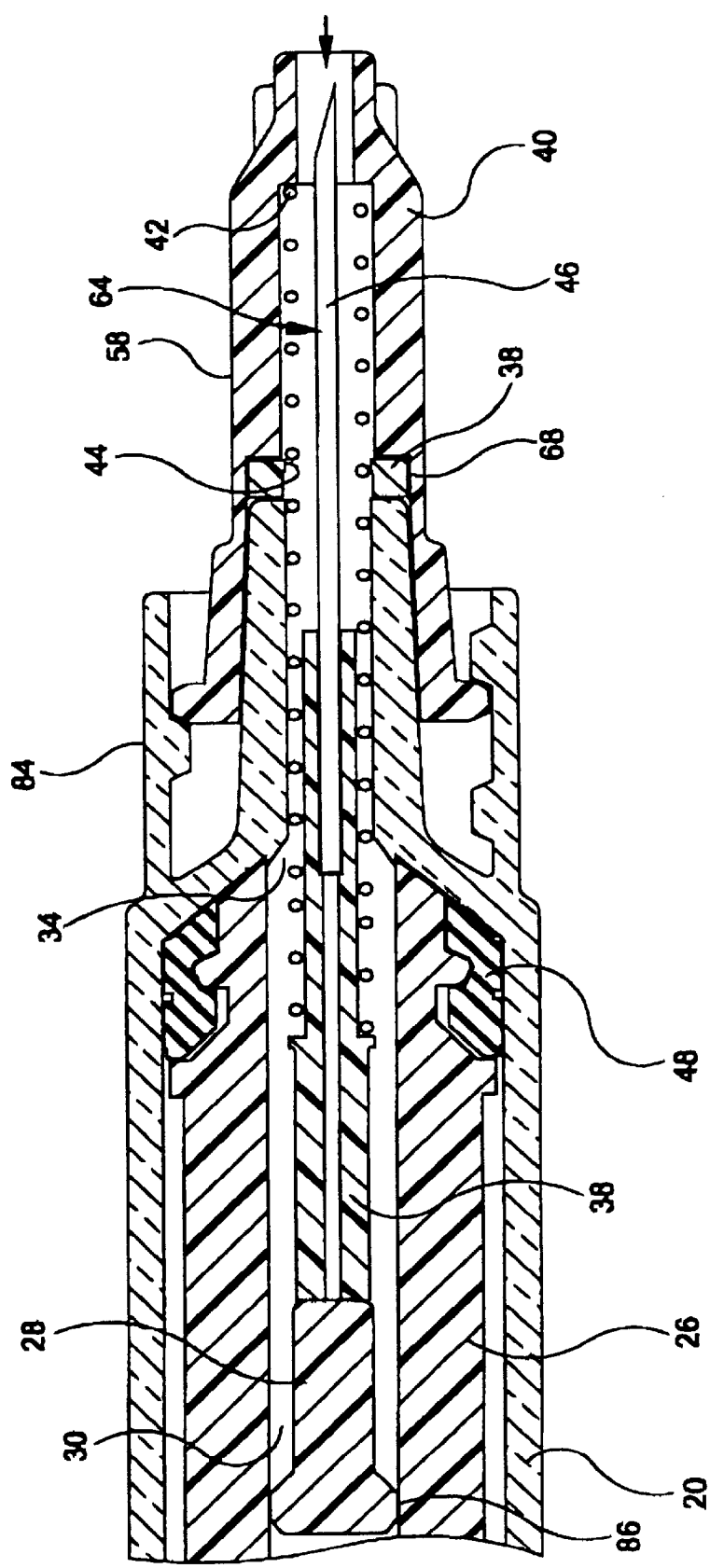
FIG. 7 is an enlarged cross-sectional view showing the function of the severing means in FIG. 6.

Severing means has various embodiments. Preferably, severing means is a frangible portion 60 surrounding the plunger tip as shown in FIG. 6. As shown in FIG. 6 and FIG. 7, the retracting needle syringe allows the piercing member to enter into the chamber. Upon fully depressing the plunger rod along the axis "A" and applying distally directed axial force to the plunger rod along axis "A," the frangible portion of the inner hub breaks and the plunger tip is dislodged by the frangible portion surrounding the plunger tip. Thus, the piercing member fixedly attached to the inner hub is allowed to enter the chamber of plunger rod. The frangible portion of the inner hub requires less force to break than the frangible portion surrounding the plunger tip such that the plunger tip breaks the frangible portion of the inner hub when the plunger rod is fully depressed. The frangible portion surrounding the plunger tip preferably breaks when it encounters the distal end of the barrel. In this case, the plunger tip would break the frangible portion of inner hub when fully depressed and upon further force in the proximal to distal direction along axis "A". Along the same axis "A", the plunger tip encounters distal end of barrel which would break frangible portion of plunger tip thereby allowing piercing member to enter the chamber. The piercing member enters the chamber by the force from the compressed spring. The frangible portion surrounding the plunger tip can also be activated by simultaneously breaking with the frangible portion of inner hub. However, this is preferably not favored because of the potential of the frangible portion of inner hub not completely breaking off. Another way to activate the frangible portion surrounding the plunger tip is after the frangible portion of the inner hub breaks, the force applied to the plunger rod is reacted by the fully compressed spring until the plunger tip is dislodged. Once the plunger tip is dislodged, and only then, the spring moves the piercing member into the plunger chamber. In all these embodiments, the end-user of the present invention supplies all the force that is necessary to break the inner hub and plunger tip while depressing the plunger rod along the same axis and direction as injection.

Also shown in FIGS. 6 and 7 is the inner hub having an inner diameter 52 and an outer diameter 54. The outer hub also has an inner diameter 56 and an outer diameter 58. The outer diameter of inner hub and inner diameter of outer hub are dimensioned to provide a permanent press-fit interface 68 between the inner hub and the outer hub. The frangible portion of inner hub allows retraction of the piercing member upon the plunger rod being fully depressed along axis "A" and when the plunger tip is dislodged by severing means then the piercing member enters the chamber.

Severing means can be either the frangible portion surrounding the plunger tip or a cutting ring 76 embedded in the distal end of the barrel as shown in FIG. 8 and FIG. 9. In the preferred embodiment, severing means is the frangible portion surrounding the plunger tip. A permanent press-fit is preferred between the outer hub and the inner hub. However, there are many ways to join these two components together such as, but not limited to, heat welding, sonic welding, snap-fits, adhesive bonding and multi-layer molding. Once these two components are joined the spring is compressed. The piercing member fixedly attached to the inner hub can only be retracted when the frangible portion of the inner hub is broken. The piercing member can only enter the chamber and thus be safety disposed of when the plunger tip is dislodged by the severing means.

Another embodiment of severing means includes the cutting ring as shown in FIGS. 8 and 9. In this alternate embodiment, the cutting ring is embedded in distal end of barrel. There are several ways to embed the cutting ring inside syringe barrel. Some of the ways of making this alternate embodiment is to hold cutting ring inside the distal end of syringe barrel by heat welding, adhesive bonding, sonic welding, frictional interference, and other methods known to one skilled in the art. Preferably, this alternate embodiment is made by insert molding cutting ring inside distal end of syringe barrel. This molding technique allows the cutting ring to be embedded in the distal end of syringe barrel without any regards of being removed. In addition, this technique allows efficiency in the assembly and production of retracting needle syringe by eliminating an assembly step. Preferably, cutting ring has a single-edge blade 78 as shown in FIG. 8 and FIG. 9.

Cutting ring 76 functions in the following manner. Upon full depression of the plunger rod along axis "A" and applying one-handed distally directed axial force to the plunger rod along axis "A" the frangible portion of inner hub breaks by the plunger tip thus unsecuring the piercing member. Upon further distally directed axial force to the plunger rod in the same direction as before, the plunger tip is dislodged by the cutting ring which is embedded in the distal end of barrel. Then, the piercing member which is fixably attached to the inner hub enters into chamber by the released force of the spring.

In this alternate embodiment, the frangible portion of inner hub requires less force to break than the plunger tip such that plunger tip breaks the frangible portion of inner hub when plunger rod is fully depressed thus unsecuring piercing member. The plunger tip is dislodged by the cutting ring upon further depression of plunger rod. The piercing member which is fixably attached to the inner hub enters the chamber by the force of spring. Also this spring action may assist in the dislodgment of the plunger tip. Although the force of spring is not required to assist in the dislodgment of the plunger tip.

Figure 3:
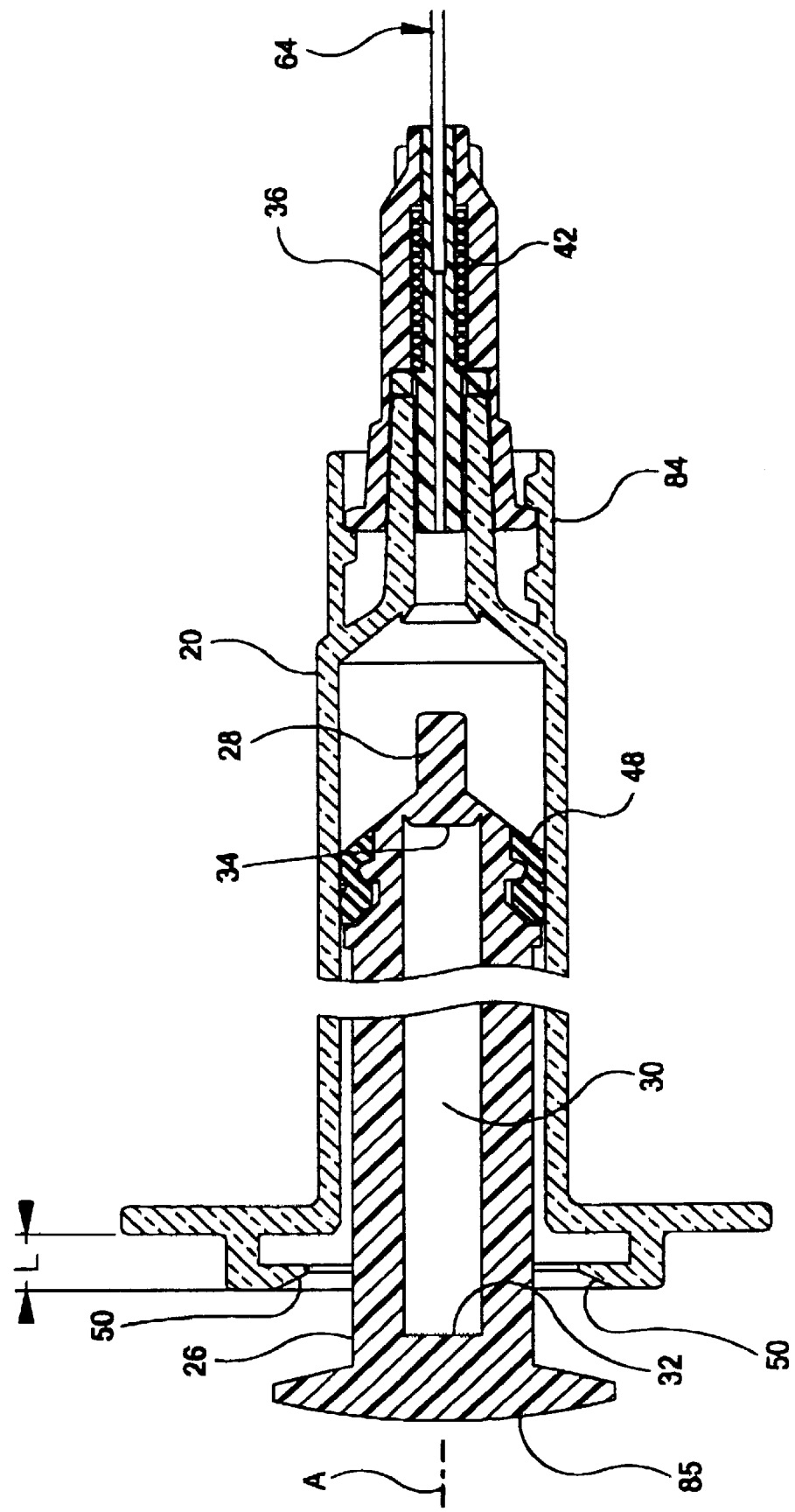
FIG. 3 is a cross-sectional view of the syringe of FIG. 1 taken along line 3—3.
Figure 4:
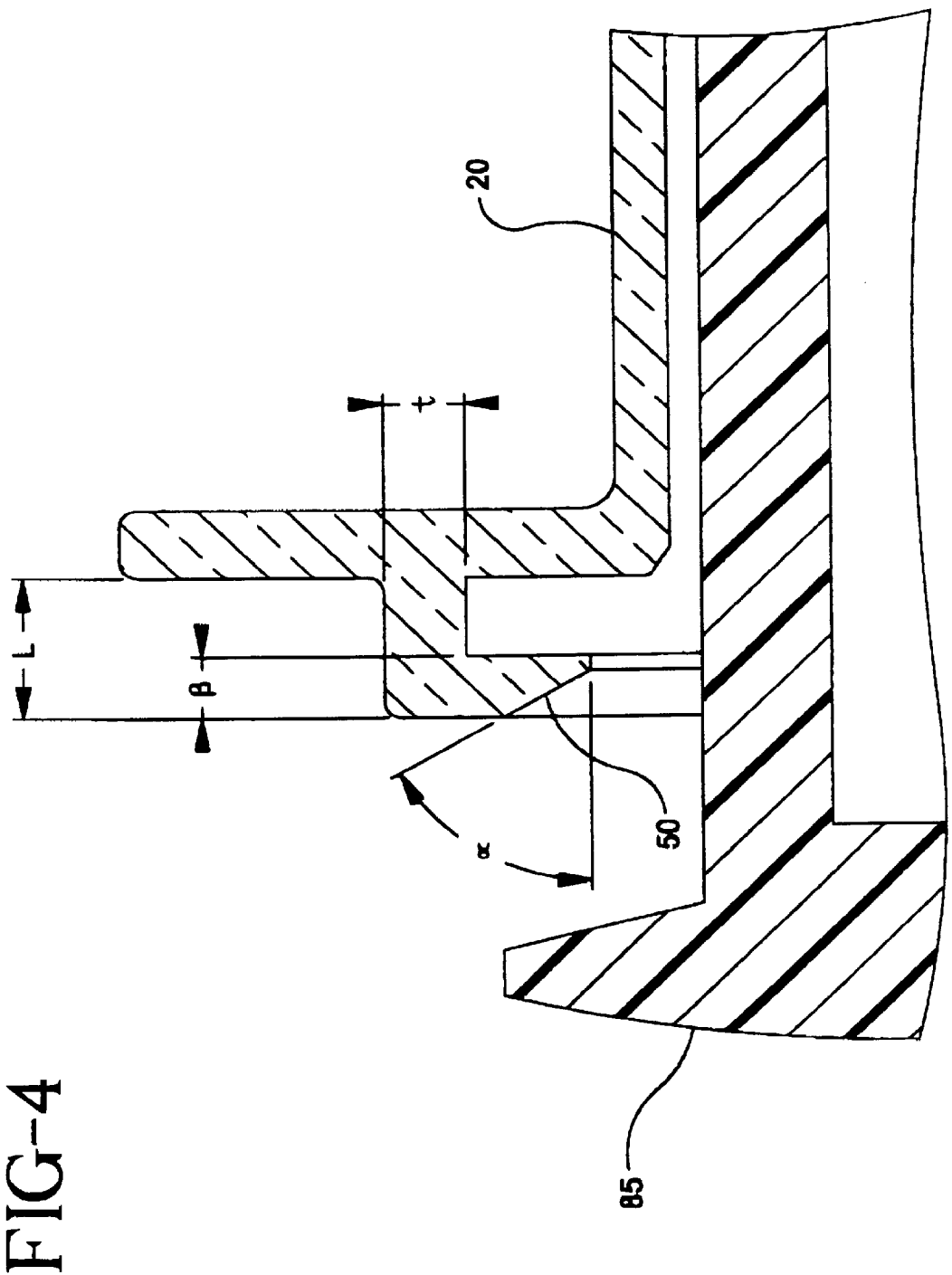
FIG. 4 is an enlarged view of FIG. 3.
Figure 5:
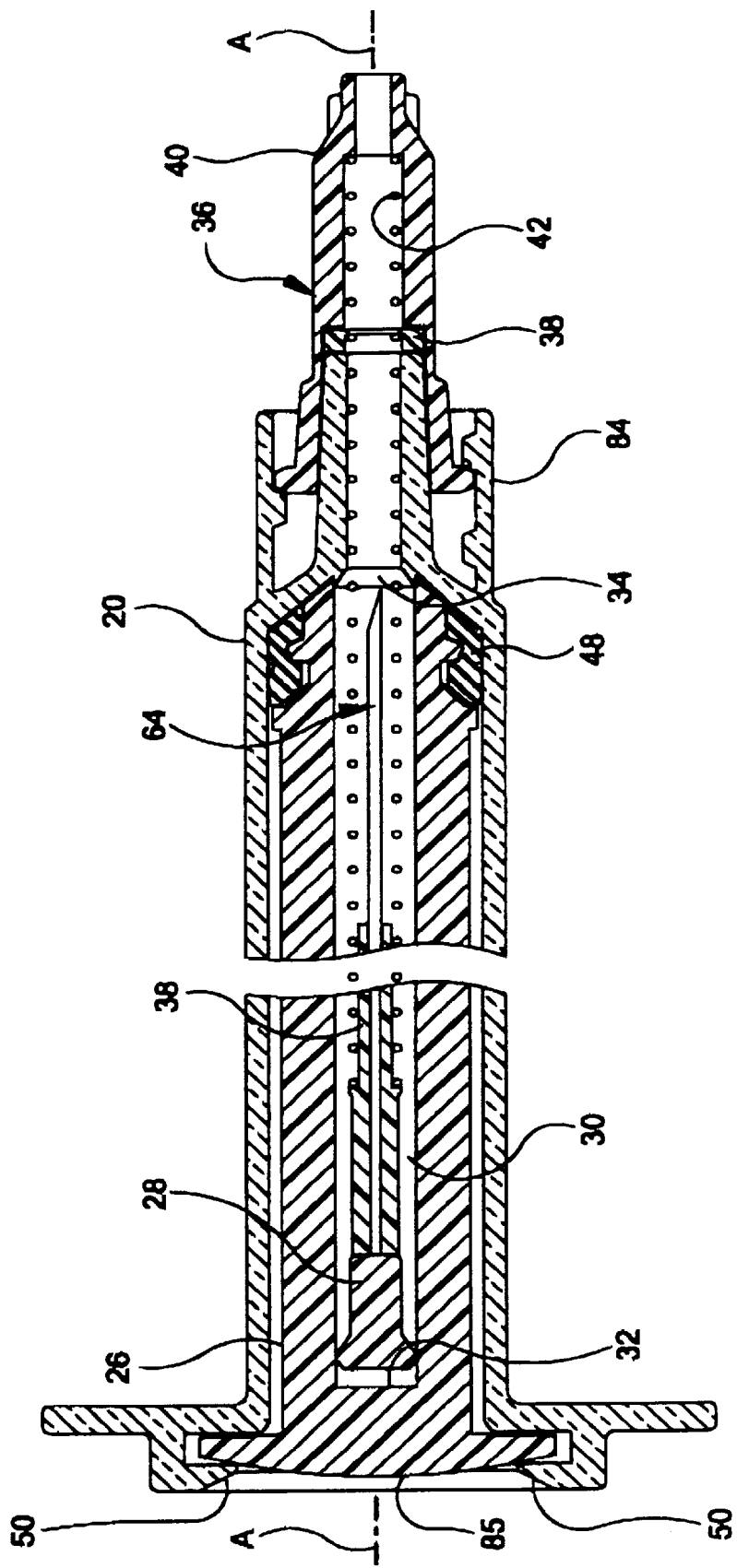
FIG. 5 is a cross-sectional view of the present invention with the plunger rod fully depressed.

Adverting to FIGS. 3, 4 and 5, a snap fitting 60 is shown on the proximal end of syringe barrel. The fitting provides for locking encapsulation of the plunger rod by the barrel alone when the plunger rod is fully depressed. This feature which also assists in preventing re-use incorporates the use of a standard thumb press 85 of the plunger rod. Thus, the fitting is in the barrel alone and does not involve any special geometry or dimensional change to the standard plunger rod thumb press. By using a standard plunger rod thumb press, efficiency in manufacturing is benefited. The snap fit has a lead-in angle α and a head width β. The snap fit also has a thickness "t" and a length "L". The snap fit provides a fast, easy and economical way to permanently lock plunger rod in the barrel. Preferably, snap fit has a tapering thickness "t" rather than a constant thickness because stress is more evenly distributed. There are several different embodiments that can provide for the encapsulation of the plunger rod in the barrel of the present invention. Some of these embodiments include torsional snap joints, annular snap joints and other cantilever snap joints.

In the case of torsional snap joints, the deflection is not the result of a flexural load as with cantilever snaps but is due to a torsional deformation of the fulcrum. The torsion bar is subject to shear. In annular snap joints, the joint can be either detachable, or inseparable, depending on the dimension of the snap joint. Inseparable designs should be avoided in annular snap joints however because of manufacturing complexity. The preferred snap joint is a cantilever-type snap joint as shown in FIGS. 3, 4 and 5 for the snap fitting. A large portion of snap joints are basically simple cantilever snaps, which may be of rectangular or of a geometrically more complex cross-section. It is preferred that the design of the snap fitting that either its thickness "t" or length "L" tapers from the root to the hook. In this way the load-bearing cross-section at any point is a more appropriate relationship to the local load. The maximum strain on the material can therefore be reduced, and less material is needed. Good results have been obtained by reducing the thickness "t" of the cantilever linearly so that its dimensional value at the end of the hook is equal to one-half the value at the root. Alternatively, the finger width may be reduced to one quarter of the base value. Special attention must be given to this area to avoid stress concentration. In all the snap fit designs that are described, it is assumed that one of the mating parts remains substantially rigid. If the two components are of approximate equal stiffness, half the deflection can be assigned to each part.

By providing the snap fitting in the present invention retracting needle syringe, the plunger rod can be completely encapsulated by the barrel alone which will prevent re-use of the syringe and allow for safe and easy disposal. The chance of reuse is also minimized by the destruction of the plunger rod and the needle assembly. Once the needle assembly is activated, it is impossible to generate positive or negative pressure in the barrel to draw up or inject the medication.

What is claimed is:

1. A retracting needle syringe, comprising:
   a syringe barrel for holding liquid, said barrel having proximal and distal ends;
   a plunger rod disposed in said barrel and having a plunger tip, and a chamber therein, said chamber having an open end sealed by said plunger tip, said plunger rod defining an axis;
   a needle assembly attached to said distal end of said barrel, said assembly having an inner hub, an outer hub, and a spring;
   said inner hub having a frangible portion and a piercing member fixably attached thereto, said spring disposed over said piercing member, said inner hub engaged inside said outer hub for providing compression to said spring; and
   severing means adjacent to said open end of said chamber for providing passage of said piercing member into said chamber through said plunger tip such that upon fully depressing said plunger rod along said axis and applying distally directed axial force to said plunger rod said frangible portion of said inner hub breaks and said plunger tip dislodges, thereby allowing said spring to move said piercing member to enter said chamber.

2. The retracting needle syringe of claim 1, wherein said needle assembly is removably attached to said end of said barrel.

3. The retracting needle syringe of claim 1, wherein the fluid in said barrel after injection is minimized by said plunger tip occupying volume in said distal end of said barrel.

4. The retracting needle syringe of claim 1, wherein said piercing member has a sharpened distal end.

5. The retracting needle syringe of claim 1, wherein said piercing member is a needle cannula.

6. The retracting needle syringe of claim 1, wherein said syringe barrel is a thermoplastic material.

7. The retracting needle syringe of claim 1, further comprising:
   a stopper attached to said plunger rod and disposed around said plunger tip such that said plunger tip is substantially uninterrupted by said stopper when said plunger tip is dislodged.

8. The retracting needle syringe of claim 1, wherein said severing means is a cutting ring in said distal end of barrel.

9. The retracting needle syringe of claim 8, wherein said cutting ring has a single edge blade.

10. The retracting needle syringe of claim 1, wherein said severing means is a frangible portion surrounding said plunger tip.

11. The retracting needle syringe of claim 1, further comprising:
    a snap fitting on said proximal end of said syringe barrel;
    said fitting providing for locking said plunger rod in said barrel when said plunger rod is fully depressed.

12. The retracting needle syringe of claim 1, wherein said inner hub comprises an outer diameter and said outer hub comprises an inner diameter, such that said outer diameter of said inner hub and said inner diameter of said outer hub are dimensioned to provide a permanent press fit between said inner hub and said outer hub, and said frangible portion of said inner hub allows retraction of said piercing member upon said plunger rod being fully depressed, and when said plunger tip is dislodged by said severing means said piecing member enters said chamber.

13. The retracting needle syringe of claim 1, wherein said frangible portion of said inner hub requires less force to break than said plunger tip such that said plunger tip breaks said frangible portion of said inner hub when said plunger rod is fully depressed and said plunger tip is dislodged by said severing means.

14. A retracting needle syringe, comprising:

a syringe barrel for holding fluid, said barrel having proximal and distal ends;

a plunger rod disposed in said barrel and having a plunger tip, and a chamber therein, said chamber having an open end sealed by said plunger tip, said plunger tip further comprising a frangible portion surrounding said plunger tip, said plunger rod defining an axis;

a needle assembly attached to said distal end of said barrel, said assembly having an inner hub, an outer hub, and a spring; and said inner hub having a frangible portion and a piercing member fixably attached thereto, said spring disposed over said piercing member, said inner hub engaged inside said outer hub for providing compression to said spring such that upon fully depressing said plunger rod along said axis and applying distally directed axial force to said plunger rod said frangible portion of said inner hub breaks and said plunger tip dislodges by said frangible portion surrounding said plunger tip, thereby allowing said spring to move said piercing member to enter said chamber.

15. The retracting needle syringe of claim 14, wherein said needle assembly is removably attached to said end of said barrel.

16. The retracting needle syringe of claim 14 wherein the fluid in said barrel after injection is minimized by said plunger tip occupying volume in said distal end of said barrel.

17. The retracting needle syringe of claim 14, wherein said frangible portion of said inner hub requires less force to break than said frangible portion surrounding said plunger tip such that said plunger tip breaks said frangible portion of said inner hub when said plunger is fully depressed and said frangible portion surrounding said plunger tip breaks when said plunger tip encounters said distal end of said barrel.

18. The retracting needle syringe of claim 14, wherein said piercing member has a sharpened distal end.

19. The retracting needle syringe of claim 14, wherein said piercing member is a needle cannula.

20. The retracting needle syringe of claim 14, wherein said syringe barrel is a thermoplastic material.

21. The retracting needle syringe of claim 14, further comprising:

a stopper attached to said plunger rod and disposed around said plunger tip such that said plunger tip is substantially uninterrupted by said stopper when said plunger tip is dislodged.

22. The retracting needle syringe of claim 14, further comprising:

a snap fitting on said proximal end of said syringe barrel; said fitting provides for locking encapsulation of said plunger rods by said barrel when said plunger rod is fully depressed.

23. The retracting needle syringe of claim 14, wherein said inner hub comprises an inner and an outer diameter and said outer hub comprises an inner and an outer diameter, such that said outer diameter of said inner hub and said inner diameter of said outer hub are dimensioned to provide a permanent press fit between said inner hub and said outer hub, and said frangible portion of said inner hub allows retraction of said piercing member upon said plunger rod being fully depressed, and when said plunger tip is dislodged by said frangible portion surrounding said plunger tip said piercing member enters said chamber.

24. A retracting needle syringe, comprising:

a syringe barrel for holding fluid, said barrel having proximal and distal ends, said barrel further comprising a cutting ring in said distal end;

a plunger rod disposed in said barrel and having a plunger tip, and a chamber therein, said chamber having an open end sealed by said plunger tip, said plunger rod defining an axis;

a needle assembly attached to said distal end of said barrel, said assembly having an inner hub, an outer hub, and a spring;

said inner hub having a frangible portion and a piercing member fixably attached thereto, said spring disposed over said piercing member, said inner hub engaged inside said outer hub for providing compression to said spring such that upon fully depressing said plunger rod along said axis and applying distally directed axial force to said plunger rod said frangible portion of said inner hub breaks and said plunger tip dislodges by action of said cutting ring, thereby allowing said spring to move said piercing member to enter said chamber.

25. The retracting needle syringe of claim 24, wherein said needle assembly is removably attached to said end of said barrel.

26. The retracting needle syringe in claim 24, wherein the fluid in said barrel after injection is minimized by said plunger tip occupying volume in said distal end of said barrel.

27. The retracting needle syringe of claim 24, wherein said cutting ring is a single edge blade.

28. The retracting needle syringe of claim 24, wherein said piercing member has a sharpened distal end.

29. The retracting needle syringe of claim 24, wherein said piercing member is a needle cannula.

30. The retracting needle syringe of claim 24, wherein said syringe barrel is a thermoplastic material.

31. The retracting needle syringe of claim 24, further comprising:

a stopper attached to said plunger rod and disposed around said plunger tip such that said plunger tip is substantially uninterrupted by said stopper when said plunger tip is dislodged.

32. The retracting needle syringe of claim 24, further comprising:

a snap fitting on said proximal end of said syringe barrel; said fitting provides for locking encapsulation of said plunger rod by said barrel when said plunger rod is fully one-handed depressed along said axis.

33. The retracting needle syringe of claim 24, wherein said inner hub comprises an inner and an outer diameter and said outer hub comprises an inner and an outer diameter, such that said outer diameter of said inner hub and said inner diameter of said outer hub are dimensioned to provide a permanent press fit between said inner hub and said outer hub, and said frangible portion of said inner hub allows retraction of said piercing member upon said plunger rod being fully depressed, and when said plunger tip is dislodged by said cutting ring said piercing member enters said chamber.

34. The retracting needle syringe of claim 24, wherein said frangible portion of said inner hub requires less force to break than said plunger tip such that said plunger tip breaks said frangible portion of said inner hub when said plunger is fully depressed and said plunger tip is dislodged by action of said cutting.

* * * * *